United States Patent [19]

Wool

[11] Patent Number: 4,952,141
[45] Date of Patent: Aug. 28, 1990

[54] HIGH VISIBILITY ORTHODONTIC ARCH WIRE SLOT

[76] Inventor: Arthur L. Wool, P.O. Box 6499, Wyomissing, Pa. 19610

[21] Appl. No.: 171,781

[22] Filed: Mar. 22, 1988

[51] Int. Cl.⁵ ............................................. A61C 3/00
[52] U.S. Cl. ........................................ 433/8; 433/3; 433/24
[58] Field of Search .................... 433/8, 9, 10, 11, 12, 433/13, 14, 15, 16, 3, 24

[56] References Cited

U.S. PATENT DOCUMENTS

| | | | |
|---|---|---|---|
| 4,134,208 | 1/1979 | Pearlman | 433/8 |
| 4,183,141 | 1/1980 | Dellinger et al. | 433/24 |
| 4,249,897 | 2/1981 | Anderson | 433/8 |
| 4,299,569 | 11/1981 | Frantz | 433/8 |
| 4,551,096 | 11/1985 | Dellinger | 433/24 |
| 4,585,413 | 4/1986 | Wool | 433/8 |
| 4,626,208 | 12/1986 | Hall | 433/3 |

FOREIGN PATENT DOCUMENTS 2903768  8/1980  Fed. Rep. of Germany .......... 433/8

Primary Examiner—John J. Wilson
Attorney, Agent, or Firm—Antonelli, Terry, Stout & Kraus

[57] ABSTRACT

An orthodontic bracket with an arch wire slot into which a high visibility marker has been inserted to facilitate alignment of the slot without the need for cumbersome jigs.

3 Claims, 1 Drawing Sheet

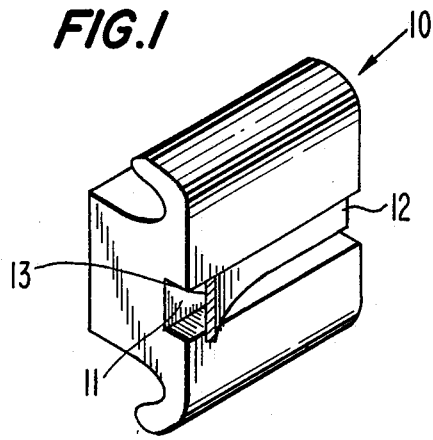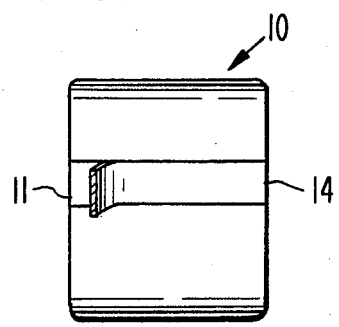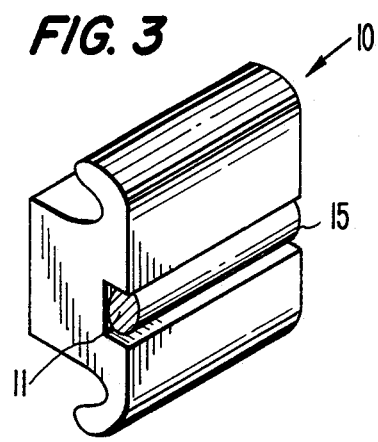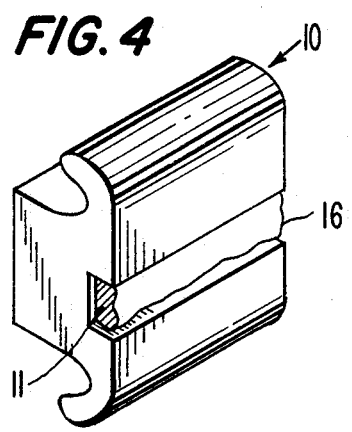

HIGH VISIBILITY ORTHODONTIC ARCH WIRE SLOT

BACKGROUND OF THE INVENTION

The present invention relates to an orthodontic arch wire slot and, more particularly, to a new and improved manner of making the arch wire slot of an orthodontic bracket more visible for greater ease of installation.

The materials with which an orthodontist works must, by necessity, be small if they are not to cause undue discomfort to the patient and fit within the acceptable confines of a patient's mouth. Such materials are shown, for example, in my U.S. Pat. No. 4,585,413. However, the need for smaller sizes runs counter to the problems of manipulation of orthodontic devices which a dentist encounters. Furthermore, it makes the tasks of seeing the components more difficult, particularly when a brace is made of transparent material or a material color which blends with the patient's teeth and this, in turn, creates the potential of improperly installing the orthodontic brace in less than an optimum position.

To overcome the problem of visibility of smaller orthodontic components, conventional techniques have been developed in an effort to increase visibility. Brackets have been marked on certain surfaces with colored dots and other indicators to indicate the direction of torque or to help the doctor differentiate right-sided, left-sided, upper and lower brackets. Removable color coded long axis indicators have been provided by Unitek Corporation in its "Transcend" brand brackets for giving a positive placement reference for the axis, with each tooth having its own color code for easy selection and identification. Color-coded identification marks can also be cast into brackets. Ormco Corporation makes color-coded vertical and horizontal placement caps for its "GEM" brand brackets and also makes metal brackets with color coded placement/identification caps for specific teeth and with different vertical displacements. I have found these products also to be more cumbersome than desired to a practicing orthodontist. Moreover, I have recognized that none of the conventional methods utilize a technique for readily aligning the arch slot in a way which will allow the arch wire to be more accurately positioned.

SUMMARY OF MY INVENTION

It is an object of my invention to overcome the problems and disadvantages encountered with prior art orthodontic brackets by making the arch wire slot more visible and thereby facilitating easier and more accurate placement and cementation of the bracket, particularly for those brackets which are transparent or of a color which blends with the patient's teeth.

I have achieved the foregoing by providing a contrasting color at the deepest wall of an arch wire slot by the use of paint or other material. In the case of paint, my invention contemplates that the paint could be removed after cementation of the bracket.

The objects and advantages of my invention can also be achieved by filling the arch wire slot with a semi-solid material having sufficient color contrast with the bracket or tooth or both and which could be brushed away or washed away after bracket cementation has occurred.

Alternatively, a small high visibility color insert made, for example, of plastic or rubber could be temporarily inserted in the slot by way of a light adhesive substance and be adapted for easy removal after cementation.

The foregoing avoids the need for cumbersome positioning jigs which encircle the bracket and have scribe lines for height placement or an L-shaped positioning jig limited to one specific height measurement.

BRIEF DESCRIPTION OF THE DRAWINGS

These and further features, objects and advantages of my invention will become more apparent from the following detailed description of the presently preferred embodiments when taken in conjunction with the accompanying drawings wherein:

FIG. 1 is a perspective view of one embodiment of my invention wherein the slot marker or high contrast color is provided an orthodontic bracket arch wire slot by pressure fit or light adhesive with a portion of the marker lifted away from the bottom of the slot as would be done after bracket cementation;

FIG. 2 shows another embodiment of my invention in the bracket in plan view wherein the marker material is in the form of a paint strip or paint rolled in the slot and which can be removed by brushing;

FIG. 3 is another embodiment of the invention in a bracket shown in perspective view wherein a colored elastomeric material such as a rubberband with high visibility coloration and slightly larger in width than the width of the arch wire slot is forced into the slot and which can be removed after bracket cementation, and FIG. 4 is yet another embodiment on which a high visibility colored material has been injected into the slot and solidified such that it can be removed by brushing out or the like after cementation has occurred.

DETAILED DESCRIPTION OF PREFERRED EMBODIMENTS

Referring now to the drawings and, in particular, to FIG. 1, there is shown an orthodontic bracket of conventional construction designated generally by the numeral 10. For ease of reference, the brackets in FIGS. 2, 3 and 4 have also been designated by the numeral 10 since they are of the same construction.

In FIG. 1, the bracket 10 has an arch wire slot 11 which accommodates an arch wire (not shown) in a known manner. A strip of material 12 having a length equal to the length of the bracket 10 and a width slightly wider than the slot 11 can be pressed into the slot 11 prior to insertion of the bracket into a patient's mouth for cementation to the appropriate tooth. In this particular instance, the bracket is shown as white and the strip 12 as having a black outer surface to provide high contrast and visibility. However, other colors may be employed as experience shows different colors to be better than other colors. Furthermore, different colors may be employed to differentiate the different teeth so that the practitioner can readily identify the appropriate brackets when they are laid out for installation. To assure that the strip 12 will remain in the slot 11 until removal is desired, the strip 12 can be provided with an adhesive 13 on the slot-contacting surface. When it is desired to remove the strip 12 after the bracket has been firmly cemented to the appropriate tooth, the orthodontist can peel out the strip 12 with a tool.

FIG. 2 shows another embodiment in which a black strip 14 which has been painted in the slot 11 of the bracket 10. The paint strip 14 can be brushed or scrapped out of the slot after cementation.

FIG. 3 shows a third embodiment in which an elastomeric material such as a black rubberband 15 having a slightly greater diameter than the width of the slot 11 can be forced into the slot and remain there until the orthodontist desires to remove it after cementation.

FIG. 4 shows a fourth embodiment in which a material 16 of high contrast color in relation to the color of the bracket 10 which has been injected into the slot 11. The material 16 can be a semi-solid and applied from a dispenser such that it subsequently hardens and can be removed by a tool. The specific material used is not essential to the present invention as long as it has a color which is high contrast to the bracket.

While I have shown several embodiments in accordance with my invention, the same is susceptible of numerous changes and modifications as will now be apparent to one skilled in this art with the benefit of the above disclosure. For example, the strip of material such as shown in FIG. 1 can be retained in the slot with a spring bias by forming the material to have a V-shaped cross section wherein the point of the "V" contacts against the bottom of the slot and each end of the legs is pressed against the walls of the slot. Alternatively, the material can assume an arcuate shape in cross-section, again with each end being springingly engaged against the walls of the archwire slot. Therefore, I do not intend to be limited to the details shown and described herein but intend to cover all such changes and modifications as are encompassed by the scope of the appended claims.

I claim:

1. An orthodontic bracket comprising a bracket body adapted to be bonded to a tooth surface, a slot provided in a face of the bracket body to receive an arch wire, and means provided in the slot to provide high contrast and visibility of the slot for alignment purposes, wherein said means is a strip having a color on one surface which is in high contrast to the bracket body and adhesive on another surface for removably securing the strip in the slot.

2. An orthodontic bracket, comprising a bracket body having an outer surface defining a profile and adapted to be bonded to a tooth surface, a slot provided in a face of the bracket body to receive an arch wire, and means provided in the slot and within the profile to provide high contrast and visibility of the slot for alignment purposes, wherein said means is a paint strip which can be selectively removed.

3. An orthodontic bracket comprising a bracket body adapted to be bonded to a tooth surface, a slot provided in a face of the bracket body to receive an arch wire, and means provided in the slot to provide high contrast and visibility of the slot for alignment purposes, wherein said means comprises an elastomeric material removably but snugly received in the slot.

* * * * *